United States Patent [19]

Mahurkar

[11] 4,134,402
[45] Jan. 16, 1979

[54] DOUBLE LUMEN HEMODIALYSIS CATHETER

[76] Inventor: Sakharam D. Mahurkar, 1926 W. Harrison St., Apt. 1809, Chicago, Ill. 60612

[21] Appl. No.: 812,901

[22] Filed: Jul. 5, 1977

Related U.S. Application Data

[63] Continuation of Ser. No. 657,282, Feb. 11, 1976, abandoned.

[51] Int. Cl.² ............................................. A61M 5/32
[52] U.S. Cl. .................................. 128/214 R; 128/221
[58] Field of Search ................ 128/214 R, 214.4, 221, 128/347, 348, 350 R, DIG. 3

[56] References Cited

U.S. PATENT DOCUMENTS

| | | | |
|---|---|---|---|
| 998,339 | 7/1911 | Hollins | 27/24 A |
| 1,290,647 | 1/1919 | Nyvall | 128/214 R X |
| 2,474,665 | 6/1949 | Guarino | 128/DIG. 3 |
| 2,564,977 | 8/1951 | Hsi Hu | 128/221 X |
| 2,590,895 | 4/1952 | Scarpellino | 128/221 |
| 2,625,932 | 1/1953 | Salisbury | 128/214.2 |
| 3,324,853 | 6/1967 | Czorny et al. | 128/214.4 |
| 3,463,152 | 8/1969 | Sorenson | 128/214.4 |
| 3,804,097 | 4/1974 | Rudie | 128/350 R |
| 4,027,668 | 6/1977 | Dunn | 128/214 R |
| 4,098,275 | 7/1978 | Consalvo | 128/214 R |

FOREIGN PATENT DOCUMENTS

| | | | |
|---|---|---|---|
| 834211 | 2/1976 | Belgium | 128/221 |
| 2259865 | 6/1974 | Fed. Rep. of Germany | 128/221 |
| 592193 | 4/1925 | France | 128/214.2 |

*Primary Examiner*—Dalton L. Truluck
*Attorney, Agent, or Firm*—Vogel, Dithmar, Stotland, Stratman & Levy

[57] ABSTRACT

A double lumen continuous flow hemodialysis needle and cannula having contiguous lumens of different lengths, the shorter lumen acting as blood intake lumen and the longer as a blood return lumen, each lumen having a beveled edge sloping outwardly and away from the needle which can be inserted percutaneously and which minimizes the possibility of mixing cleansed blood with blood entering the intake lumen.

7 Claims, 9 Drawing Figures

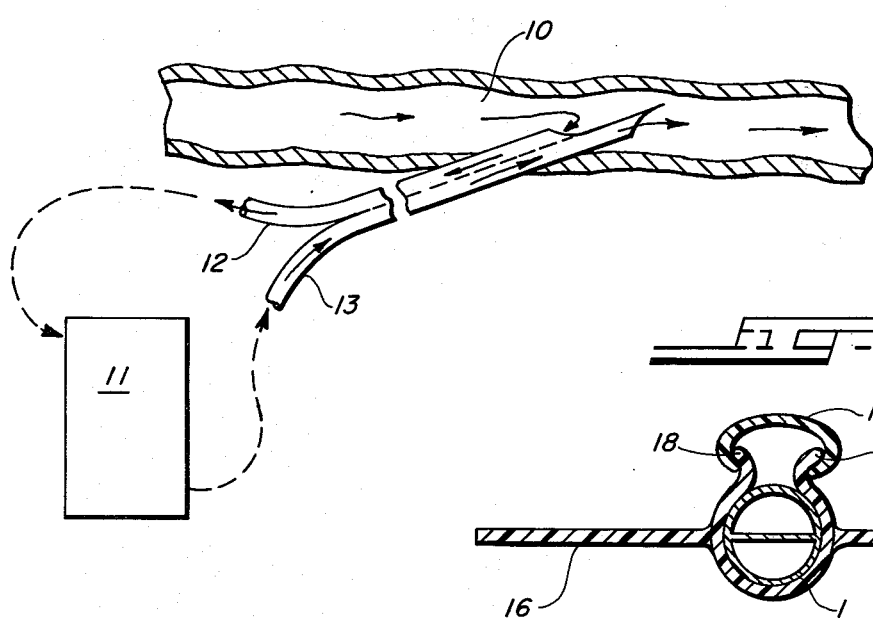

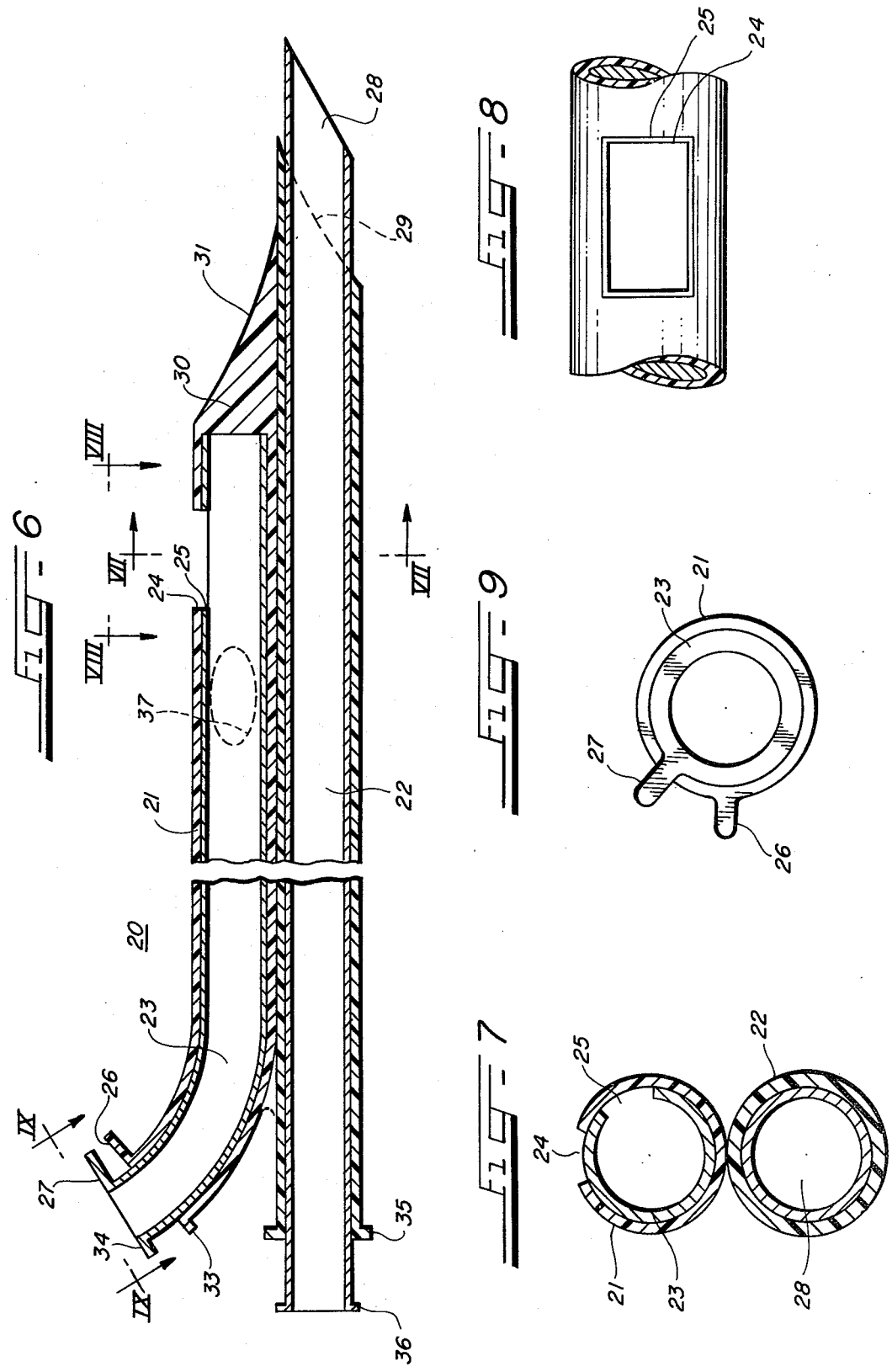

DOUBLE LUMEN HEMODIALYSIS CATHETER

RELATED APPLICATIONS

This is a continuation of application Ser. No. 657,282, filed Feb. 11, 1976 now abandoned.

BACKGROUND OF THE INVENTION

This invention relates to a catheter primarily for use in hemodialysis and more specifically, to a hemodialysis catheter having a double lumen.

Hemodialysis is currently performed two basic ways. First, the conventional way employing two needles, one for removing the blood from the fistula or vein for processing in a dialysis machine and the other needle for returning processed blood back into the fistula or vein. In this conventional technique for hemodialysis, the two needles must be spaced apart a sufficient distance so as to prevent the cleansed blood from re-entering the blood outlet needle and returning to the dialysis machine but must be sufficiently close to each other to prevent the vein or fistula from collapsing.

A second known manner of performing hemodialysis utilizes a single needle in which blood is both extracted and returned through the same needle. However, single needle dialysis requires an intermittent occlusion machine which is capable of the cyclical operation necessitated by the single lumen needle with bi-directional flow. In addition, single needle dialysis can only operate within limited flow rates and accordingly is not suitable for all patients.

For repeated dialysis requirements, a method utilizing two long tubes of unequal length attached side by side is also known. In such a method the tubes are introduced into the femoral vein after surgery and remain there for several days during which hemodialysis is performed intermittently.

Accordingly, it is the primary object of the present invention to provide a double lumen catheter for hemodialysis capable of achieving blood flow rates comparable to the conventional two needle system while requiring only one puncture.

It is a further object of the present invention to provide a double lumen catheter capable of use with a conventional hemodialysis machine.

Yet another object of the present invention is to provide a double lumen catheter which can be easily inserted percutaneously for treatment and easily removed after each dialysis treatment.

Other objects and advantages of the invention will become apparent upon reading the following detailed description and upon reference to the attached drawings.

SUMMARY OF THE INVENTION

Briefly stated, the present invention consists of a single catheter having two contiguous lumens or coaducts, one slightly longer than the other. The needle is generally inserted into the vein or fistula at a slight angle to and in the direction of blood flow. The shorter lumen then serves as a blood intake lumen and the longer lumen, the end of which is positioned away from the end of the shorter lumen in the direction of blood flow, serves as a blood return lumen. With this arrangement, cleansed blood returning to the vein or fistula will not re-enter the intake lumen but will be carried "downstream".

BRIEF DESCRIPTION OF THE DRAWINGS

FIG. 1 is an illustration of a double lumen needle of the present invention;

FIG. 2 is a cross section along the lines II — II;

FIG. 3 is a cross section along the lines III — III;

FIG. 4 is a schematic showing blood flow during hemodialysis;

FIG. 5 is a cross section along the lines V — V;

FIG. 6 is a flexible double lumen catheter according to the present invention;

FIG. 7 is a cross section along the lines VII — VII;

FIG. 8 is a cross section along the lines VIII — VIII; and,

FIG. 9 is an end view along the lines IX — IX.

DESCRIPTION OF THE PREFERRED EMBODIMENT

Referring to FIG. 1 it can be seen that the present invention consists of a single catheter 1 having lumens 2 and 3. The term "catheter" as used in this specification includes rigid metal devices such as needles as well as flexible plastic devices such as a cannula. As illustrated in FIG. 1, the end of lumen 3 extends beyond the end of lumen 2 a sufficient distance to prevent mixing of the blood during the hemodialysis operation. The precise distance by which lumen 3 extends beyond lumen 2 is determined by the rate of blood flow in the vein or fistula, the angle of entrance of the double lumen needle, and the size of the vein or fistula. Strictly by way of example, for an average fistula, (i.e., a surgically constructed blood vessel with rapid blood flow rates) having a diameter of ⅛ inch and processing blood at approximately 500 cubic centimeters per minute, the separation "d" FIG. 1 would be approximately ¼ inch. This separation could be as large as ¾ inch under appropriate conditions.

In the preferred embodiment each lumen is provided with beveled edges at 4 and 5 sloping outwardly and away from the needle to promote insertion of the needle. It is preferable for return lumen 3 to be of semi-circular cross section near its end (FIG. 2). In the region where they are contiguous, the lumens define a compact cross section (FIG. 3). Lumen 2 preferably defines a semi-circular cross section along its entire length. It is also preferable to provide an aperture 32 near the tip of lumen 2 so that blood will continue to flow through this opening even if beveled edge 4 becomes obstructed.

Referring to FIG. 3, it can be seen that in the region where the lumens are contiguous the lumens are separated by a wall 6. This wall 6 can be relatively thin construction inasmuch as its only function is to separate the blood return conduit 8 from the blood intake conduit 9. The wall 7, in contrast, must serve as a supporting wall and accordingly must be of heavier construction.

Turning now to FIG. 4, the actual operation will be described with reference to a double lumen needle constructed in accordance with the present invention. The double lumen needle 1 is inserted into the vein or fistula 10 at a slight angle in the direction of blood flow. The noninserted ends of the lumens are connected to a dialysis machine 11. This connection can be accomplished by separating the lumens 1, 2 into two noncontiguous polyethylene stabilizer tubes 12, 13 (FIG. 1) of circular cross section with standard luer ends so that conventional coupling members may be utilized. With the machine in operation, blood flows from the vein or fistula into lumen 2 via outwardly sloping beveled edge 4 to the dialysis machine 11 where blood is processed. The blood is then returned to the vein or fistula through lumen 3 at a sufficient pressure to overcome the natural resistance to the returning blood. Referring to FIG. 4 it can be seen that the returning blood enters the vein or fistula at a point displaced some distance away from the point where blood enters intake lumen 2 does so via outwardly sloping beveled 4 and in the direction of blood flow in the vein or fistula. The blood flow through the fistula or vein then carries this processed blood away from re-entering intake lumen 2.

In order to aid in inserting the needle and in order to permit rotation of the needle after insertion to achieve optimal blood flow, a rotably mounted double mast assembly 14 is provided. When the double lumen needle is inserted it may have to be rotated or moved slightly inwardly or outwardly in order to achieve optimum blood flow because of the bevelled edges 4, 5 may be too close to the wall of the vein or fistula. Accordingly, it is preferable to provide an adjustable securing means such as the double mast assembly 14.

In practice, the mast assembly is locked against rotational movement by sliding spring clip 15 over the tabs 18, 19. The masts are then pinched together between the thumb and forefinger just as with a conventional single lumen needle fixed mast assembly. After insertion the mast assembly is unlocked by removing spring clip 15 and the needle is rotated until the desired blood flow is achieved. The mast assembly 14 is again locked in place by sliding spring clip 15 over tabs 18, 19. The downward facing surfaces 16, 17 are then pressed firmly against the skin and secured by tape or other adhesive.

While the foregoing description applies to a rigid catheter; i.e., a "needle", the present invention is also applicable to flexible catheters constructed of teflon or the like. Such a catheter is commonly referred to as a cannula. Referring to FIG. 6, the present invention as applied to a flexible catheter will be described.

The flexible catheter 20 consists of two tubular contiguous lumens, 21 and 22. Rotably and slideably interposed in lumen 21 is blood intake lumen 23. Lumens 21 and 23 are provided with intake ports 24 and 25 respectively. By rotating lumen 23 the intake port 25 can be aligned with intake port 24 in order to permit blood flow or lumen 23 can be rotated to achieve disalignment of ports 24, 25 (FIG. 7) to prevent blood flow. Lumens 21 and 23 are provided with standard female luer ends 33, 34 respectively. Indexing means can also be provided to index the aligned port position as shown in FIGS. 7 and 9 where indexing tabs 26, 27 are provided at the ends of lumens 21, 23 respectively on the luer ends.

The procedure for inserting the flexible double lumen catheter will now be described. With intake ports 24, 25 in the disaligned position (FIGS. 7 and 9) a hypodermic needle 28 having female luer end 36 is inserted through lumen 22 having female luer end 35 so as to protrude past the end 29 of lumen 22. With the hypodermic needle thus protruding, the double lumen catheter is inserted into the vein or fistula at a slight angle to and in the direction of blood flow; the skin being punctured by the needle 28. The solid terminal portion 30 of lumen 21 is preferably provided with a bevelled tip 31 to promote insertion. When the double lumen catheter is fully inserted, the hypodermic needle 28 is withdrawn and the intake ports 24, 25 are aligned rotating indexing tab 27 to coincide with tab 26 (FIG. 9). Therefore blood does not enter intake lumen 23 until the catheter is fully inserted. Accordingly, the possibility of blood clotting — a troublesome possibility with flexible catheters which are used primarily in the femoral thigh vein and thus must be approximately six inches long — is greatly minimized. With the catheter fully inserted and the intake ports aligned, the catheter is adjusted if necessary by rotating advancements or withdrawal to achieve satisfactory blood flow. Lumen 23 is then withdrawn and lumen 21 is then coupled to a dialysis machine by conventional methods. Blood then flows through port 24, through lumen 21, through the machine and then returns to the femoral vein by way of blood return port 29 through

I claim:

1. A double lumen hemodialysis catheter, comprising a unitary straight tube the periphery of which in transverse cross section defines a single closed plane curve at any point along the entire straight tube, an internal divider extending along a longitudinal portion of said tube and forming said tube into a blood intake lumen and a blood return lumen, one end of said blood return lumen extending beyond the associated end of said blood inlet lumen a distance sufficient to prevent mixing of the returned blood with the blood taken in, the one end of said blood return lumen being beveled with the extending from the lumen periphery opposite said divider and rearward of the distal end toward the distal end and said divider, the associated end of said blood inlet lumen being beveled with the bevel extending from the lumen periphery opposite said divider and rearward of the associated distal end toward the associated distal end and said divider, the distal end of said blood inlet lumen terminating rearward of the juncture of the blood return lumen bevel and the associated lumen periphery each of said lumens defining blood flow paths parallel one to the other along the entire length thereof and at the ends thereof such that blood entering said intake lumen and blood leaving said return lumen enter and exit the associated blood vessel in a direction substantially parallel to the vessel wall.

2. The invention as claimed in claim 1, wherein said blood inlet lumen bevel terminates at said divider rearward of said blood return bevel intersection with said tube periphery.

3. The invention as claimed in claim 1 wherein the end of the blood return lumen extends beyond the end of the blood intake lumen at least one-quarter inch but no greater than three-quarter inch.

4. The invention as claimed in claim 1 wherein the intake lumen is provided with an aperture at its side near its end.

5. A double lumen hemodialysis catheter comprising: a first blood intake lumen having a blood intake port, a second blood intake lumen rotatably and removably interposed in said first lumen and having a blood intake port, means for rotating said second lumen so as to align said intake ports, a blood return lumen contiguous with said first and second lumens the end of said blood return lumen extending beyond the blood intake port of the first blood intake lumen a sufficient distance to prevent returning blood from re-entering said blood intake ports, said blood return lumen having a beveled end sloping outwardly and away from the catheter, so that the catheter can be inserted by a single puncture for continuous bi-directional blood flow.

6. The invention as claimed in claim 5 wherein the end of the blood return lumen extends between one inch and three inches past the blood intake port of the first blood intake lumen.

7. The invention as claimed in claim 5 further comprising indexing means for aligning said intake ports.

* * * * *

UNITED STATES PATENT AND TRADEMARK OFFICE
CERTIFICATE OF CORRECTION

PATENT NO. : 4,134,402
DATED : January 16, 1979
INVENTOR(S) : Sakharam D. Mahurkar It is certified that error appears in the above-identified patent and that said Letters Patent are hereby corrected as shown below:

Column 1, line 58, "coa" should be --con--.
Column 3, line 64, after "aligned" should be --by--.
Column 4, line 11, after "through" insert --return lumen 22 which is coupled to the machine using conventional methods.

For a femoral vein in a normal adult the separation "d" (FIGURE 6) between blood intake port 24 and blood return port 29 can range from 1 inch to 3 inches. It is also preferable to provide an aperture 37 in lumen 21 near blood intake port 24 so that blood flow will continue even if port 24 is blocked. When dialysis is finished, the flexible double lumen catheter is removed.--;
line 22, after "the" insert --bevel--.

Signed and Sealed this

Seventeenth Day of April 1979

[SEAL]

Attest:

RUTH C. MASON
Attesting Officer

DONALD W. BANNER
Commissioner of Patents and Trademarks

REEXAMINATION CERTIFICATE (1101st)

United States Patent [19]

Mahurkar

[11] B1 4,134,402

[45] Certificate Issued Jul. 25, 1989

[54] DOUBLE LUMEN HEMODIALYSIS CATHETER

[76] Inventor: Sakharam D. Mahurkar, 1926 W. Harrison St., Apt. 1809, Chicago, Ill. 60612

Reexamination Request:
No. 90/001,319, Aug. 31, 1987

Reexamination Certificate for:
Patent No.: 4,134,402
Issued: Jan. 16, 1979
Appl. No.: 812,901
Filed: Jul. 5, 1977

Related U.S. Application Data

[63] Continuation of Ser. No. 657,282, Feb. 11, 1976, abandoned.

[51] Int. Cl.$^4$ .................................... A61M 5/32
[52] U.S. Cl. .................... 604/44; 604/248; 604/249; 604/272
[58] Field of Search .............. 604/43, 44, 272–274, 604/280–284

[56] References Cited

U.S. PATENT DOCUMENTS

| | | | |
|---|---|---|---|
| 256,590 | 4/1882 | Pfarre . | |
| 390,177 | 9/1988 | Lee . | |
| 701,075 | 5/1902 | McCully . | |
| 998,339 | 7/1911 | Hollins | 27/24 A |
| 1,045,326 | 11/1912 | Ruflin . | |
| 1,093,538 | 4/1914 | Clough . | |
| 1,290,647 | 1/1919 | Nyvall | 128/214 R X |
| 1,922,084 | 8/1933 | Gerow | 128/349 |
| 2,175,726 | 10/1939 | Gebauer | 128/349 B |
| 2,230,218 | 2/1941 | Asche | 128/276 |
| 2,234,961 | 3/1941 | Canada | 128/327 |
| 2,409,343 | 10/1946 | Curtis | 128/214 |
| 2,473,742 | 6/1949 | Auzin | 128/349 |
| 2,474,665 | 6/1949 | Guarino | 128/DIG. 3 |
| 2,564,977 | 8/1951 | Hu | 128/221 X |
| 2,590,895 | 4/1952 | Scarpellino | 128/221 |
| 2,625,932 | 1/1953 | Salisbury | 604/44 |
| 2,716,983 | 9/1955 | Windischman et al. | 128/221 |
| 2,819,718 | 1/1958 | Goldman | 128/350 |
| 2,930,378 | 3/1960 | Buyers | 128/354 |
| 3,042,045 | 7/1962 | Sheridan | 128/349 |
| 3,175,554 | 3/1965 | Stewart | 128/2 |
| 3,314,430 | 4/1967 | Alley et al. | 128/350 |
| 3,324,853 | 6/1967 | Czorny et al. | 128/214.4 |
| 3,324,854 | 6/1967 | Weese | 128/215 |
| 3,331,371 | 7/1967 | Rocchi et al. | 128/349 |
| 3,359,974 | 12/1967 | Khalil | 128/2.05 |
| 3,394,705 | 7/1968 | Abramson | 128/349 |
| 3,435,826 | 1/1969 | Fogarty | 128/348 |
| 3,437,088 | 4/1969 | Bielinski | 128/2 |
| 3,448,739 | 6/1969 | Stark et al. | 128/2.05 |
| 3,452,756 | 7/1969 | Harautuneian | 128/349 |
| 3,459,188 | 7/1965 | Roberts . | |
| 3,463,152 | 8/1969 | Sorenson | 128/214.4 |
| 3,467,101 | 9/1969 | Fogarty et al. | 128/348 |
| 3,543,758 | 12/1970 | McWhorter | 128/349 |
| 3,543,759 | 12/1970 | McWhorter | 128/349 |
| 3,550,591 | 12/1970 | MacGregor | 128/214.4 |
| 3,556,161 | 1/1971 | Roberts . | |
| 3,566,874 | 3/1971 | Sheperd et al. | 128/349 |
| 3,593,713 | 7/1971 | Bogoff et al. | 128/246 |
| 3,599,620 | 8/1971 | Balin | 128/349 B |
| 3,612,050 | 4/1972 | Sheridan . | |
| 3,634,924 | 1/1972 | Blake et al. | 29/447 |
| 3,683,908 | 8/1972 | Michael et al. | 128/145.7 |
| 3,726,281 | 4/1973 | Norton et al. | 128/349 R |
| 3,746,003 | 7/1973 | Blake et al. | 128/349 B |
| 3,756,234 | 9/1973 | Kopp | 128/214 R |
| 3,771,527 | 11/1973 | Ruisi | 128/350 R |
| 3,774,605 | 11/1973 | Jewett | 128/214.4 |
| 3,799,172 | 3/1974 | Szpur | 128/349 R |
| 3,804,097 | 4/1974 | Rudie | 128/350 R |
| 3,823,720 | 7/1974 | Tribble | 128/350 R |
| 3,828,767 | 8/1974 | Spiroff | 128/2.05 |
| 3,830,234 | 8/1974 | Kopp | 128/214 R |
| 3,875,938 | 4/1975 | Mellor | 128/214.4 |
| 3,885,567 | 5/1975 | Ross | 128/278 |
| 3,896,815 | 7/1975 | Fettel et al. | 128/348 |
| 3,978,863 | 9/1976 | Fettel et al. | 128/348 |
| 4,004,588 | 1/1977 | Alexander | 128/241 |
| 4,016,879 | 4/1977 | Mellor | 128/214.4 |
| 4,027,668 | 6/1977 | Dunn | 128/214 R |
| 4,037,599 | 7/1977 | Raulerson | 128/214.4 |

FOREIGN PATENT DOCUMENTS

| | | | |
|---|---|---|---|
| 834211 | 2/1976 | Belgium | 128/221 |
| 935625 | 11/1955 | Fed. Rep. of Germany . | |
| 2259865 | 6/1974 | Fed. Rep. of Germany | 128/221 |
| 592193 | 4/1925 | France | 128/214.2 |
| 1285953 | 7/1962 | France . | |
| 1508959 | 1/1968 | France . | |
| 2285148 | 4/1976 | France . | |
| 2297640 | 8/1976 | France . | |
| 688450 | 3/1952 | United Kingdom . | |
| 1419702 | 12/1975 | United Kingdom | 128/221 |
| 1503469 | 10/1976 | United Kingdom . | |

OTHER PUBLICATIONS

McIntosh et al., "Double Lumen Catheter," *J.A.M.A.*, Feb. 21, 1959, pp. 137/835–138/836.

Reus et al., "Double-Lumen Catheter in Extracorporeal Hemodialysis," Archives of Internal Medicine, Apr. 26, 1963, pp. 523–525.

*Dorland's Illustrated Medical Dictionary*, 25th Ed., W. B. Saudners Co., Philadelphia, 1974, p. 274.

Tohoku J. exp. Med., 1974, 114, 189–191 (Short Report) "Single Two-Lumen Cannula Dialysis", Tsuchida et al.

Tsuchida et al., "Design of a Two-Lumen-Piercing Needle That Is Capable of Carrying Out Dialysis by Single Puncture", Journal of the Urological Society of Japan, vol. 65 (12), 1974, pp. 805–807.

Brenner & Rector, *The Kidney*, vol. III, W. B. Saunders Co., Philadelphia, 1976, p. 164.

*ASAIO Abstracts*, vol. 5, 22nd Annual Meeting, San Francisco, California, Apr. 1–3, 1976, p. 52.

Nihon Hinyoskika Gakkai Zasshi, vol. 65, No. 12, (1974), pp. 805–807; "A Two Lumen Puncture Needle With Which Dialysis is Possible By Single Puncture", Tsuchida et al, (long report) with Certified English Translation.

Journal of the American Medical Association, Feb. 21, 1959, vol. 169, pp. 835-836, "Double Lumen Catheter For Use With Artificial Kidney", McIntosh et al.

*Primary Examiner*—Dalton L. Truluck

[57] ABSTRACT

A double lumen continuous flow hemodialysis needle and cannula having contiguous lumens of different lengths, the shorter lumen acting as blood intake lumen and the longer as a blood return lumen, each lumen having a beveled edge sloping outwardly and away from the needle which can be inserted percutaneously and which minimizes the possibility of mixing cleansed blood with blood entering the intake lumen.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–7 is confirmed.

* * * * *